United States Patent
Stormbom

[11] Patent Number: 5,987,963
[45] Date of Patent: Nov. 23, 1999

[54] METHOD OF IMPROVING THE SELECTIVITY OF A POLYMER-FILM GAS SENSOR AND A SENSOR STRUCTURE FOR IMPLEMENTING THE METHOD

[75] Inventor: Lars Stormbom, Vantaa, Finland

[73] Assignee: Vaisala Oy, Helsinki, Finland

[21] Appl. No.: 08/988,896

[22] Filed: Dec. 11, 1997

[30] Foreign Application Priority Data

Dec. 13, 1996 [FI] Finland .................................. 965015

[51] Int. Cl.⁶ .................................................. G01N 27/00
[52] U.S. Cl. .......................... 73/25.01; 73/23.2; 73/25.05
[58] Field of Search .................................. 73/23.2, 25.01, 73/25.05

[56] References Cited

U.S. PATENT DOCUMENTS 5,288,645  2/1994  Toshima et al. .................... 73/19.01 X
5,625,139  4/1997  Stormborm ........................... 73/23.21

FOREIGN PATENT DOCUMENTS

0075101A3  8/1982  European Pat. Off. .
0092068A1  3/1983  European Pat. Off. .
2218523A   11/1989  United Kingdom .

*Primary Examiner*—Daniel S. Larkin
*Attorney, Agent, or Firm*—Birch, Stewart, Kolasch & Birch, LLP

[57] ABSTRACT

The invention relates to a method for improving the selectivity of a polymer film gas sensor. According to the method, the gas sensor is heated and a sensor parameter sensitive to the variable under measurement is recorded. According to the invention, the parameter of the sensor sensitive to the variable under measurement is measured at a plurality of instants during both the heating period and the cooling period of the sensor, a hysteresis function of the sensor response is formed over the heating and cooling periods, and on the basis of the hysteresis function, the concentration of each measured gas component is determined.

3 Claims, 2 Drawing Sheets

METHOD OF IMPROVING THE SELECTIVITY OF A POLYMER-FILM GAS SENSOR AND A SENSOR STRUCTURE FOR IMPLEMENTING THE METHOD

BACKGROUND OF THE INVENTION

1. Field of the Invention

The present invention relates to a method according to the preamble of claim 1 for improving the selectivity of a polymer-film gas sensor.

The invention also concerns a sensor structure.

The present invention is particularly suited for extracting the specific signal of a single gas component from a composite signal representing at least one other gas component interfering strongly with the applied gas measurement technique.

2. Description of Background Art

A polymer-film gas sensor is characterized by being sensitive to a plurality of different gas species. A typical approach to improve sensor selectivity has been sought from a combination of several gas sensors of different types and then interpreting the output signals of such a sensor combination by means of, e.g., a neural network. However, this kind of a measurement system becomes complicated and costly.

Also known in the art are arrangements in which the polymer-film sensors are heated in order to restore their original properties in a manner described in, e.g., FI Pat. Appl. 942,727. While this technique is capable of restoring the sensor performance, the basic selectivity of the gas sensor under a normal measurement situation cannot be improved.

It is an object of the present invention to overcome the drawbacks of the above-described prior-art technique and to provide an entirely novel method for improving the selectivity of a polymer-film gas sensor.

SUMMARY AND OBJECTS OF THE INVENTION

The goal of the invention is achieved by heating the sensor and measuring over the entire heating/cooling cycle a sensor parameter known to be sensitive to the variable under measurement, whereby the measurement performed during the cycle is plotted into a hysteresis function, wherefrom the variable under measurement can be resolved.

The principal advantage of the invention is that gas components interfering with the measurement can be excluded from the measurement result with high efficiency and at a low cost.

Another significant benefit of the novel measurement method is that, in a gas-free environment, the sensor always exhibits a zero hysteresis irrespective of its possible aging behaviour.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, the invention will be examined in greater detail with the help of exemplifying embodiments illustrated in the appended drawings which are given by way of illustration only, and thus are not limitative of the present invention, and wherein.

DETAILED DESCRIPTION OF THE PREFERRED EMBODIMENT

The measurement method according to the invention utilizes the different characteristic diffusion time constants of different gas components for discriminating between the gas components involved in the measurement. As known, the diffusion of gas components becomes exponentially accelerated with a rising temperature. Simultaneously, the amount of gas absorbed under equilibrium conditions in the polymer layer is reduced.

However, if the polymer layer is heated rapidly, the amount of gas absorbed in the layer will not reach an equilibrium, but rather, an excess amount of gas remains in the layer. This excess amount of gas will remain in the layer until the diffusion constant of the gas reaches a sufficiently high value with the increase of the temperature.

As different gases have also different diffusion constants, the time to reach an equilibrium is different for different gases at different temperatures.

Figure 1:
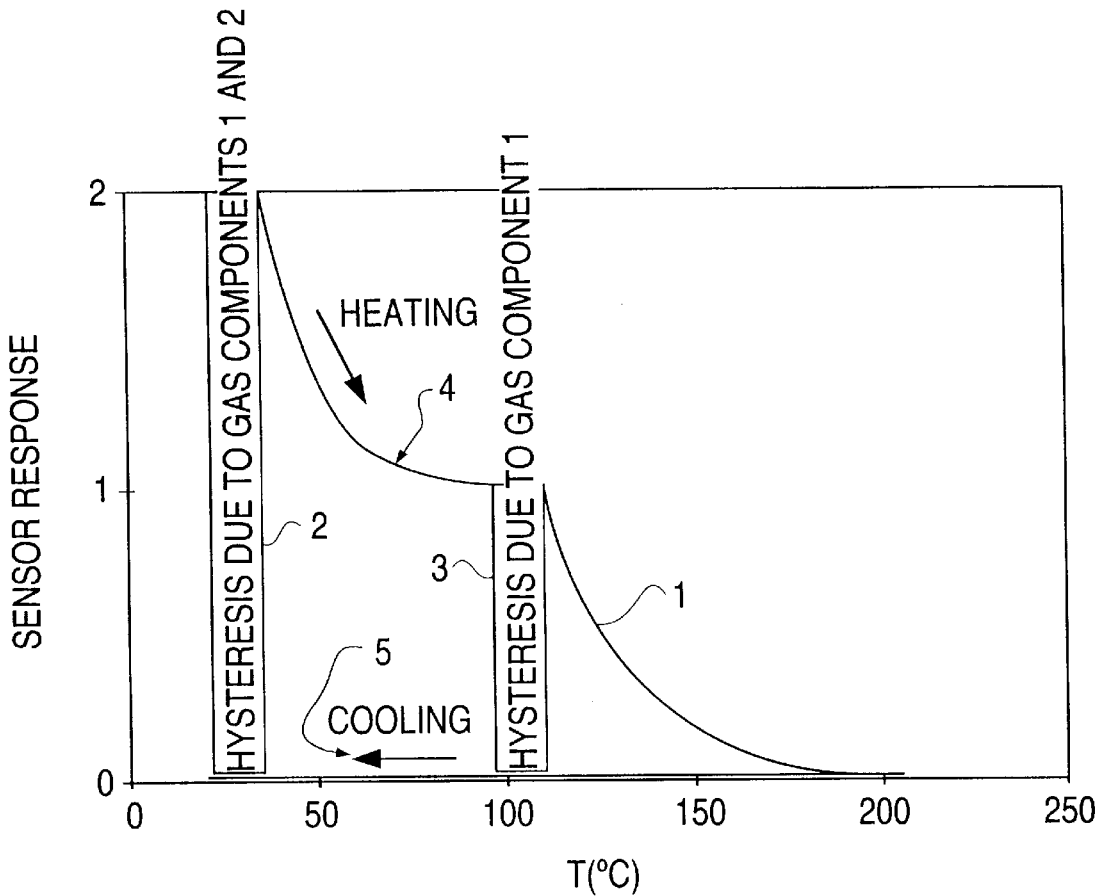
FIG. 1 shows a graph of a typical measurement cycle recorded by the method according to the invention.

As shown in FIG. 1, the heating of the polymer layer of the gas sensor to a temperature sufficiently high (100–200° C.) above the ambient temperature, allows practically all gas components to be expelled from the polymer layer.

When performed sufficiently quickly after the heating period, cooling of the layer can keep it free from absorbed gases down to the ambient temperature.

Based on these facts, a function 1 of the sensor response function vs. temperature exhibiting a hysteresis can be recorded by measuring simultaneously the sensor response to a variable, for which the polymer-film gas sensor is designed (whereby the recorded parameter can be, e.g., sensor capacitance, conductivity, or weight), and the sensor temperature over both a heating period 4 and a cooling period 5. In other words, the function characterizing the sensor response at a given temperature has during the heating period a value different from that of the cooling period.

This variation, known as hysteresis, of the response function decreases at higher temperatures. At the lowest temperature, the hysteresis 2 is caused by all the gas components collectively. When the temperature of the polymer layer is elevated, the gas with the highest diffusion coefficient is expelled first, whereby its contribution in the sensor response disappears. Continued elevation of the layer temperature expels the gas component of the second highest diffusion coefficient as shown at point 3 of the diagram, etc.

By measuring the loop of the hysteresis function 1 over two or more temperature spans, the sensor response to different gas components can be differentiated. The concentrations of the gas components may be determined from the minima and maxima of the derivative of the hysteresis function, or alternatively, from the points of discontinuity in the hysteresis function.

To achieve the reabsorption of the gas components back into the polymer layer, a sufficiently long equilibrating period must be arranged between the successive measurement cycles.

The active polymer layer of the sensor 6 can be self-supported or bonded to a substrate. Typically, the layer thickness is in the range 0.1–10 μm. The heating and cooling rates of the polymer layer are typically in the range 10–1000° C./s.

In an alternative embodiment of the present invention, the sensor is heated only to sufficiently high temperature to expel the gas component interfering with the measurement but not so high as to expel the gas component under measurement (that is, gas component 1 in the diagram involving hysteresis loop 3). This arrangement permits a faster repetition rate of the successive measurement cycles. As compared to the first embodiment of the method, herein the value of the sensor response under gas-free conditions at the measurement temperature must be known.

Obviously, the above-described hysteresis values may be complemented with intermediate values of the measured sensor parameter recorded at a given temperature over the heating period or the cooling period.

Additional information can be obtained by performing two measurement cycles rapidly in succession, whereby the gas component of slow diffusion cannot reach equilibrium by diffusing back into the sensor. Herein, the parameters to be recorded could be, e.g., the change in the hysteresis function between the two successive measurements.

Figure 2:
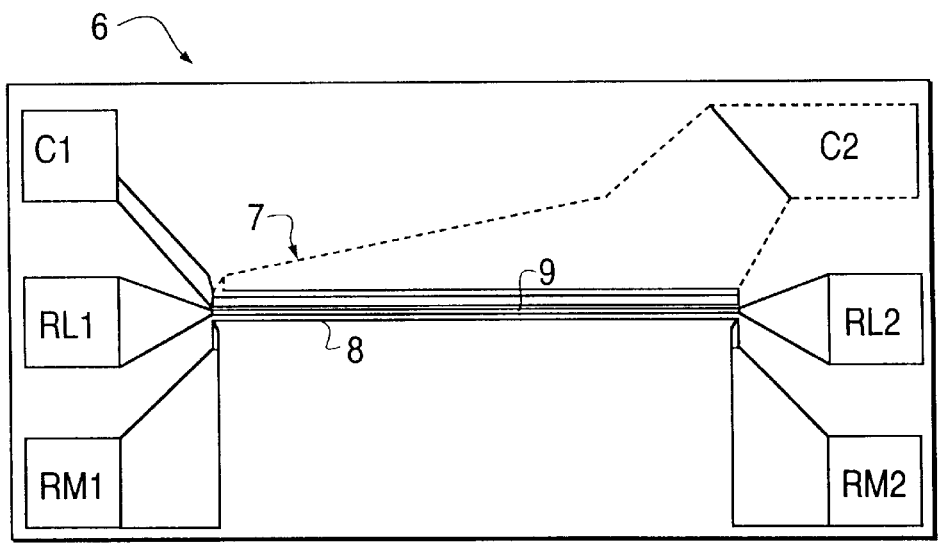
FIG. 2 shows a schematic top view of a sensor structure suited for implementing the method according to the invention.

Now referring to FIG. 2, an exemplifying embodiment of the sensor structure 6 is shown therein. The sensor chip size is 7×3.5×0.4 mm (made from glass, for instance, which due to its low thermal conductivity is not an ideal material). The gas measurement signal is the capacitance of the capacitor 7, measured over contacts C1–C2 (about 100 pF). The sensor 6 is heated by means of heater element 9 connected over contacts RL1–RL2 (about 100 ohm). The sensor temperature is measured by means of another resistor 8 connected over contacts RM1–RM2 (about 300 ohm). The thermal coefficient of the resistor 8 is typically about 3000 ppm/° C.

The sensor capacitance 7 and the temperature sensing resistor 8 are located maximally symmetrical with respect to the heater element 9, thus assuring that their temperature tracks the sensor temperature during a fast temperature change.

A typical heating/cooling cycle is performed as follows:
1. The heating voltage applied over contacts RL1–RL2 is ramped linearly up from 0 V to 10 V during 400 ms.
2. The heating voltage is kept at 10 V for 300 ms.
3. The heating voltage is ramped linearly down to 0 V during 400 ms.

During the cycle, the sensor capacitance and the resistance of its temperature sensor are measured at a rate higher than 25 times a second.

Figure 3:
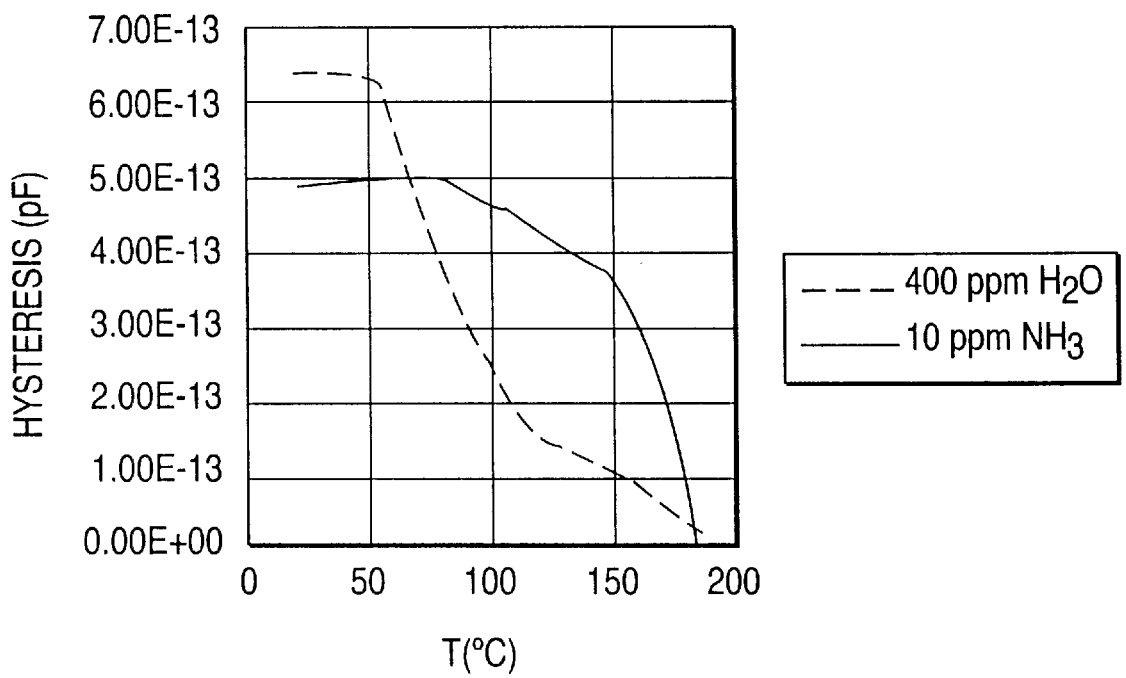
FIG. 3 shows a graph of measurement cycles performed for two different gases according to the invention.

As shown in FIG. 3, the concentrations of water vapour ($H_2O$) and ammonia gas ($NH_3$) are determined from the maxima of the derivative of the hysteresis function, whereby water vapour shows a maximum at 60° C. while ammonia gas is detected from the maximum of the derivative at 160° C.

The maxima/minima of the derivative of the hysteresis function may also be utilized for determination of different types of gases.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What I claim is:

1. A method for improving the selectivity of a polymer-film gas sensor, wherein the gas sensor is heated and a sensor parameter sensitive to the variable under measurement is recorded, the method comprising the steps of:

measuring the parameter of the sensor sensitive to the variable under measurement at a plurality of instants during both the heating period and the cooling period of the sensor;

forming a hysteresis function of the sensor response over the heating and cooling periods; and determining, on the basis of the hysteresis function, the concentration of each measured gas component.

2. A method as defined in claim 1, wherein the concentration of the measured gas component is determined on the basis of minima and maxima in the derivative of the said hysteresis function.

3. A method a defined in claim 1, wherein the value of the measured sensor parameter is recorded at a rate higher than 25 times a second.

* * * * *